United States Patent

Davis

[11] Patent Number: 6,059,723
[45] Date of Patent: *May 9, 2000

[54] FIBEROPTICALLY ILLUMINATED TONGUE DEPRESSOR

[76] Inventor: James M. Davis, 4687 Pond Apple Dr. South, Naples, Fla. 33999

[*] Notice: This patent issued on a continued prosecution application filed under 37 CFR 1.53(d), and is subject to the twenty year patent term provisions of 35 U.S.C. 154(a)(2).

[21] Appl. No.: 09/006,722

[22] Filed: Jan. 14, 1998

Related U.S. Application Data

[60] Provisional application No. 60/035,518, Jan. 15, 1997.

[51] Int. Cl.[7] .................................................. A61B 1/06
[52] U.S. Cl. ............................................ 600/241; 600/245
[58] Field of Search .......................... 600/245, 240, 600/241, 248, 246, 212, 223, 199; 362/119, 572, 573

[56] References Cited

U.S. PATENT DOCUMENTS

| | | | |
|---|---|---|---|
| 849,209 | 4/1907 | Crawford | 600/248 |
| 2,247,258 | 6/1941 | Shepard | 600/241 |
| 3,349,764 | 10/1967 | Edinger et al. | 600/241 |
| 3,397,687 | 8/1968 | Kirchdoerfer | 600/240 |
| 3,774,614 | 11/1973 | Cook | 600/245 |
| 3,848,587 | 11/1974 | McDonald | 600/241 |
| 4,090,506 | 5/1978 | Pilgrim | 600/248 |
| 4,562,832 | 1/1986 | Wilder et al. | 600/245 |
| 4,567,030 | 6/1986 | Brody et al. | 600/245 |
| 4,605,990 | 8/1986 | Wilder et al. | 600/245 |
| 4,807,599 | 2/1989 | Robinson et al. | 600/241 |
| 4,996,976 | 3/1991 | Nakagawa | 600/241 |
| 5,156,604 | 10/1992 | Hessel et al. | 600/245 |
| 5,318,009 | 6/1994 | Robinson | 600/241 |

*Primary Examiner*—Paul J. Hirsch
*Attorney, Agent, or Firm*—William E. Noonan

[57] ABSTRACT

A fiberoptically illuminated medical appliance, and in particular, an illuminated tongue depressor includes a light conducting blade, at least a portion of which is light projecting. The blade includes a light inlet that is operably engaged with the outlet of an optical fiber. The opposite inlet end of the optical fiber is operably interengaged with a fiberoptic illuminator.

7 Claims, 1 Drawing Sheet

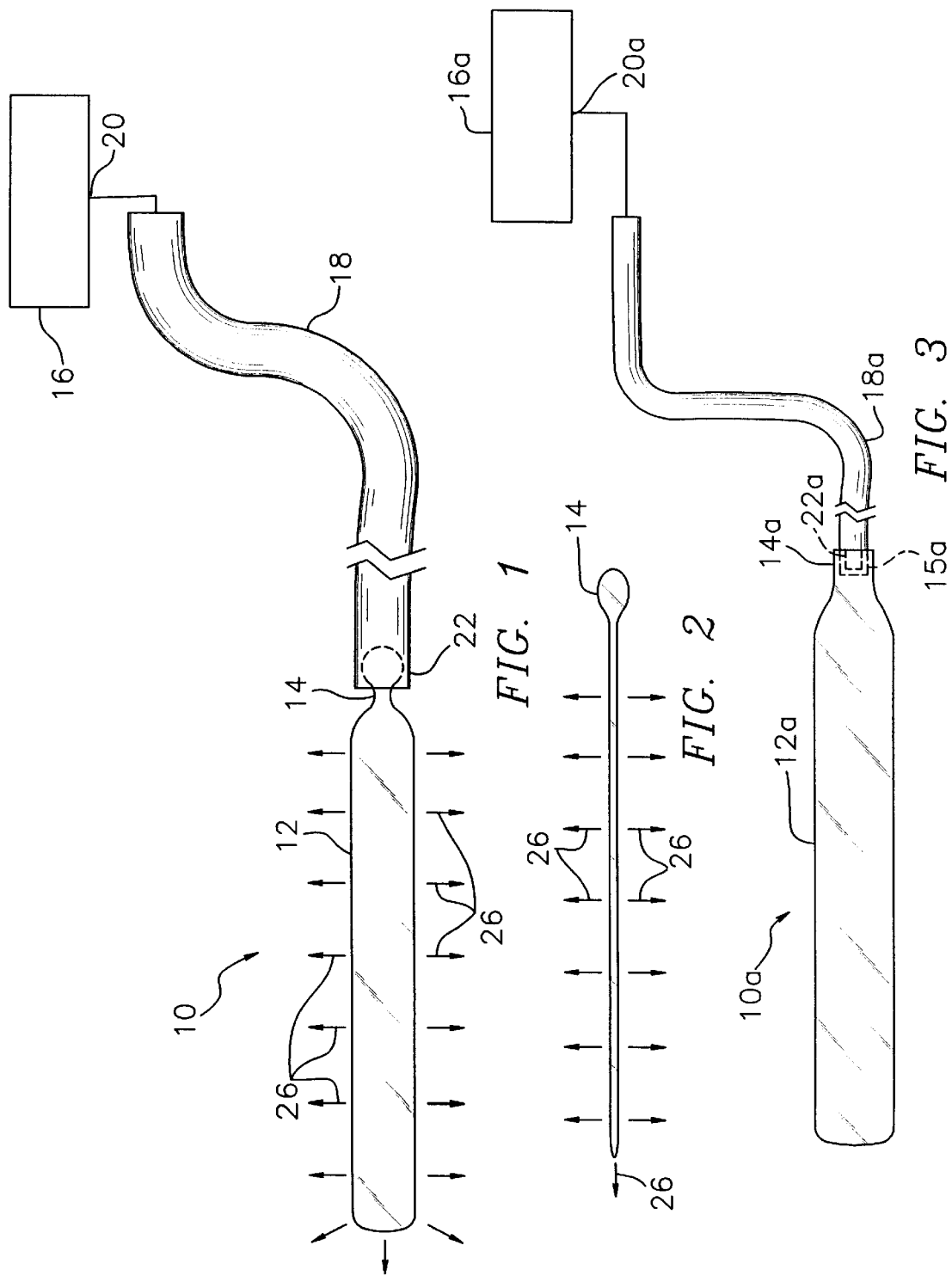

FIBEROPTICALLY ILLUMINATED TONGUE DEPRESSOR

RELATED APPLICATION

This application claims the benefit United States Provisional Patent Application Ser. No. 60/035,518, filed Jan. 15, 1997.

FIELD OF THE INVENTION

This invention relates to a fiberoptically illuminated medical appliance and, more particularly, to a disposable tongue depressor that is engagable with a fiberoptic light source to illuminate the interior of a patient's mouth.

BACKGROUND OF THE INVENTION

Doctors and dentists often have a difficult time properly illuminating an area of the patient upon which a medical procedure is being performed. Overhead lamps often do not provide adequate lighting. Moreover, such lamps usually require constant adjustment, which must be performed either by the physician or an assistant. This can disrupt the medical procedure. In recent years, fiberoptic illuminators have been widely used. These instruments typically feature a headlamp that is worn by the doctor or dentist and tethered by a fiberoptic cable to a light source. Physicians often dislike wearing an item that ties or tethers them to another instrument. Such an arrangement restricts the freedom of movement during the medical procedure. Furthermore, utilizing standard fiberoptic illumination systems requires the purchase and introduction of expensive and sometimes bulky equipment into the medical or dental office.

One example of a procedure that is awkward to properly illuminate is the standard depression of the tongue for visual examination of a patient's throat, tonsils, and adjacent areas. For many years this procedure has been performed by the use of a standard tongue depressor. The physician holds the tongue depressor in one hand and holds a light in the other hand. Alternatively, the illuminated head lamps, discussed above, may be employed. In either case, disadvantages are experienced. If the physician is required to hold a light in one hand, both hands are occupied and focusing the light properly may be difficult. A headlamp is difficult to focus properly and tethers the physician to an illuminator as described above. In either case, the interior of the mouth is not optimally illuminated.

SUMMARY OF INVENTION

It is therefore an object of this invention to provide a fiberoptically illuminated medical appliance that conducts and projects light simply and effectively on a desired area of the patient without requiring the incorporation of single or multiple fiber light channels on the appliance itself, or other standard fiberoptic illumination equipment.

It is a further object of this invention to provide illuminated medical appliance that does not restrict the physician's movements and which does not require constant repositioning by the physician.

It is a further object of this invention to provide a fiberoptically illuminated medical appliance that illuminates an area of the body being worked upon without requiring constant monitoring or adjustment by the physician and without distracting the physician's attention from the medical procedure.

It is a further object of this invention to provide a fiberoptically illuminated medical appliance that consolidates both the function of the appliance and illumination of the particular area of the body being worked upon.

It is a further an object of this invention to provide a fiberoptically illuminated medical appliance that consolidates medical equipment and minimizes the amount and volume of such equipment that is required.

It is a further an object of this invention to provide a fiberoptically illuminated tongue depressor that projects light into a patient's mouth with much greater intensity, focus and effectiveness than is accomplished by the prior art.

It is a further an object of this invention to provide a fiberoptically illuminated tongue depressor that is relatively inexpensive, readily disposable and easy to assembly, disassemble and replace such that each successive patient is provided with a fresh appliance.

It is a further an object of this invention to provide a fiberoptically illuminated tongue depressor that frees the physician from having to hold a separate light pointed at the patient's mouth, thereby freeing at least one of the physician's hands for other tasks.

This invention results from a realization that significantly improved efficiency and simpler lighting of medical procedures is achieved by employing the medical appliance as a light conductor and projector, without requiring a specific single or multiple fiber channel to conduct light from a point where the cable attaches to the medical appliance. This invention results from the further realization that oral examinations are significantly improved by employing a tongue depressor that is attached to a fiberoptic light source and that conducts and transmits light into the interior of the oral cavity.

This invention features a fiberoptically illuminated medical appliance. The appliance includes a flexible blade that is composed of a light conductive material. At least a portion of the blade of the medical appliance projects light. The appliance includes optical inlet means that are optically attached to the blade and communicably interconnected with complementary means at one end of a fiberoptic conductor. The other end of the fiberoptic conductor is operably engaged with a light source. Light from the light source is transmitted through the fiberopic conductor to the medical appliance. The medical appliance conducts light to the light projecting portion. Light is projected from the light projecting portion toward the area of the blade upon which the medical procedure is being performed.

In a preferred embodiment, the entire medical appliance may comprise a light projecting material. The inlet portion may include a male element that is interengaged with a fiberoptic conductor. Alternatively, the inlet may comprise a receptacle or other female element that communicably and operably receives the fiberoptic conductor. The male member may include a rounded or bulbous element. The optical inlet means is preferably unitarily attached to the blade.

The medical appliance preferably comprises a tongue depressor. The tongue depressor may include a transparent, plastic material. Light may be emitted or projected along the entire length of the tongue depressor.

DETAILED DESCRIPTION OF PREFERRED EMBODIMENTS

Other objects, features and advantages will occur from the following description of preferred embodiments and the accompanying drawings, in which:

FIG. 1 is a top, partly schematic view of a preferred fiberoptically illuminated tongue depressor according to this invention;

FIG. 2 is an elevational side view of the tongue depressor; and

FIG. 3 is a top, partly schematic view of an alternative illuminated tongue depressor having a slotted inlet for receiving a fiberoptic conductor.

There is shown in FIG. 1 a fiberoptically illuminated tongue depressor appliance 10 that is used to illuminate the interior of a patient's mouth during an examination of the throat and oral cavity. Appliance 10 includes a disposable tongue depressor blade 12. The tongue depressor blade comprises an elongate piece of transparent, light conducting plastic material. As shown in FIG. 2, blade 12 is substantially flat. A rounded or bulbous element 14 is formed at one end and defines a light inlet for the blade. Blade 12 should include a lightweight and inexpensive flexible material and should be capable of being operated in a conventional manner to hold a patient's tongue in place. The plastic material comprising the tongue depressor blade should be appropriate for use in the patient's mouth.

The blade is releasably interconnected to a conventional fiberoptic illuminator device 16. The illuminator comprises a standard fiberoptic illuminator commonly used in medical procedures and having a halogen, neon or other known type of light source. Illuminator 16 is operably interconnected to blade 12 by a light conducting tube or fiber 18. The optical fiber includes a first end 20 that is interengaged with illuminator 16 by means of a plug or other known fiberoptic connecting component. The opposite end 22 of fiber 18 receives and operably interengages bulbous inlet 14 of blade 12. Fiber end 22 defines a light outlet which transmits light from fiber 18 to inlet 14 of blade 12.

In operation, illuminator 16 is activated so that light is transmitted through fiber 18. This light is then transmitted through inlet 14 into blade 12. The entire outer surface of the tongue depressor blade comprises a light projecting material. As a result, light is emitted from the blade as indicated by arrows 26 in FIGS. 1 and 2. In certain embodiments, the outer surface of the blade may be frosted to reduce the glare of emitted light 26.

The physician introduces tongue depressor blade 12 into the patient's mouth, engages the tongue and holds it down in a standard manner. At the same time, light is projected from the blade into the interior of the patient's mouth and the oral cavity is brightly illuminated. The physician can then fully and properly examine the mouth and throat. He or she is not required to hold an examination light in the other hand. Overhead lighting adjustments are eliminated, as are fiberoptic headlamps. The annoying interruptions, distractions and restrictions that these implements normally introduce into the procedure are thereby eliminated.

To effectively transmit the light from fiber 18 through tongue depressor blade 12, the blade should be composed of a material that effectively conducts light along the entire length of the depressor and at the same time permits light to be dispersed laterally from the blade. Various light conductive materials may be utilized for this purpose.

A particular beneficial feature of this invention is the disposability of tongue depressor blade 12. The blade is mass produced through a conventional molding process, which minimizes the manufacturing time and expense. A flexible, light conducting plastic should be employed. Various sizes and shapes of depressors may be utilized and particular dimensions are not a limitation of this invention. However, typically, the tongue depressor blade will be generally elongate and flat, as shown in the drawings. After each use, the blade is quickly and easily detached from fiber 18, disposed of and replaced with a new blade, which is fitted into the open end 22 of tubular fiber 18. Although disposability is preferred, in certain embodiments, a more permanent tongue depressor blade, which is sterilized between patients, may be utilized.

An alternative illuminated tongue depressor appliance 10a is illustrated in FIG. 3. Appliance 10a includes an elongate, flexible tongue depressor blade 12a. 12a. The blade again comprises a transparent, light conducting and light projecting material. The primary difference between depressor blade 12a and the previously described tongue depressor blade is the use of a female inlet 14a. This inlet includes a slot or receptacle 15a that receives an outlet end 22a of optical fiber 18a. The optical fiber is operably interconnected at its opposite end 20a to a standard illuminator 16a.

In operation, light is directed from illuminator 16a through optical fiber 18a. This light is transmitted from outlet end 22a to depressor inlet 14a. The light is then conducted though and projected from blade 12a in a manner similar to that previously described.

It should be understood that in certain embodiments of this invention, light is projected from only a portion of the medical appliance. To accomplish this, the tongue depressor should be composed of a material that effectively conducts light along the length of the body of the appliance, but does this will a minimum of radial light loss. A transparent material may be employed and a coating or frosting may be applied to the outer surface of the transparent material to minimize diffusion and dispersion of the light. In such cases a portion (typically at the distal or terminal end of the appliance) does not carry the coating and acts as a light projector. In still other embodiments, the coating may be entirely eliminated and a transparent, light conducting material that inherently exhibits minimal radial light dispersion may be used. Likewise, in this embodiment, a distal or other portion of the medical appliance should exhibit a light projecting capability.

In all versions of this invention, significant advantages are achieved. Both the function of the tongue depressor and lighting are consolidated into a single piece of equipment. Constant lighting adjustments are avoided.

The physician's or dentist's attention is not distracted and, often times, the need for an assistant is eliminated. This invention also reduces the need for separate pieces of medical lighting equipment. The operation of the dental and medical office is thereby greatly simplified.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. A fiberoptically illuminated tongue depressor comprising:

an elongate and substantially flat blade that is selectively engaged with an interior portion of a person's mouth, said blade having an interior composed exclusively of a continuously solid, one-piece light conducting material and an outer surface composed of a light projecting material;

an elongate fiberoptic conductor having a first end that is interconnected to a standard fiberoptic light source and a second end from which light from the fiberoptic light source is emitted; and an optical inlet unitarily connected to said blade, said second end of said fiberoptic conductor being communicably, releasably, intimately and directly connected coupled to said optical inlet such that one of said conductor and said inlet is plugged into the other of said conductor and said inlet to deliver light from said light source through said inlet to said blade, whereby light is transmitted intrinsically, both longitudinally and laterally through said light conducting solid material of said blade to said outer surface of said blade, such that said outer surface projects light into and illuminates the person's mouth.

2. The device of claim 1 in which said blade includes a pair of generally planar surfaces that are generally parallel to one another.

3. The device of claim 1 in which said optical inlet include a male member that is received by an opening in said second end of said fiberoptic conductor.

4. The device of claim 1 in which said optical inlet comprise a receptacle that communicably and operably receives said fiberoptic conductor.

5. The device of claim 1 in which said blade is a transparent, plastic material.

6. A fiberoptically illuminated tongue depressor for use in combination with a fiberoptic light source and an elongate fiberoptic conductor, which conductor has a first end that is operably interconnected to the light source and an opposite second end from which light from the light source is emitted, said tongue depressor comprising:

an elongate and substantially flat blade that is selectively engaged with an interior portion of a person's mouth, said blade having an interior composed exclusively of a continuously solid, one-piece light conducting material and an outer surface composed exclusively of a light projecting material; and an optical inlet unitarily connected to said blade, said second end of said fiberoptic conductor being communicably, releasably, intimately and directly connected coupled to said optical inlet such that one of said conductor and said inlet is plugged into the other of said conductor and said inlet to deliver light from said light source through said inlet to said blade, whereby light is transmitted intrinsically, both longitudinally and laterally through said light conducting solid material of said blade to an outer surface of said blade such that the entire outer surface projects light into and illuminates the person's mouth.

7. A fiberoptically illuminated tongue depressor comprising:

an elongate, substantially flat blade that is selectively engaged with an interior portion of a person's mouth, said blade being composed exclusively of a continuously solid, one-piece light conducting and projecting material; and an elongate fiberoptic conductor having a first end that is interconnected to a standard fiberoptic light source and a second end from which light from the fiberoptic light source is emitted; and an optical inlet unitarily connected to said blade, said second end of said fiberoptic conductor being communicably, releasably, intimately and directly connected coupled to said optical inlet such that one of said conductor and said inlet is plugged into the other of said conductor and said inlet to deliver light from said light source through said inlet to said blade, whereby light is transmitted intrinsically, both longitudinally and laterally through said light conducting solid material of said blade to an outer surface of said blade, which outer surface projects light into and illuminates the person's mouth.

* * * * *